United States Patent
Storm, Jr. et al.

(10) Patent No.: US 6,748,328 B2
(45) Date of Patent: Jun. 8, 2004

(54) DETERMINING FLUID COMPOSITION FROM FLUID PROPERTIES

(75) Inventors: Bruce H. Storm, Jr., Houston, TX (US); Mark A. Proett, Missouri City, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 10/166,195

(22) Filed: Jun. 10, 2002

(65) Prior Publication Data
US 2003/0229448 A1 Dec. 11, 2003

(51) Int. Cl.⁷ ................................................. G01V 1/40
(52) U.S. Cl. ........................................ 702/6; 73/152.16
(58) Field of Search .............................. 702/6; 250/256, 250/255, 253, 269.1; 73/152.41, 290 R, 152.28; 507/100; 367/73

(56) References Cited

U.S. PATENT DOCUMENTS

| | | | | |
|---|---|---|---|---|
| 4,994,671 A | * | 2/1991 | Safinya et al. | 250/255 |
| 5,266,800 A | * | 11/1993 | Mullins | 250/256 |
| 5,331,156 A | * | 7/1994 | Hines et al. | 250/256 |
| 5,518,996 A | * | 5/1996 | Maroy et al. | 507/100 |
| 5,519,214 A | * | 5/1996 | Houwen et al. | 250/256 |
| 5,644,076 A | * | 7/1997 | Proett et al. | 73/152.41 |
| 5,741,962 A | * | 4/1998 | Birchak et al. | 73/152.28 |
| 6,350,986 B1 | * | 2/2002 | Mullins et al. | 250/269.1 |
| 6,378,364 B1 | * | 4/2002 | Pelletier | 73/152.47 |
| 6,539,795 B1 | * | 4/2003 | Scherpenisse et al. | 73/290 R |

FOREIGN PATENT DOCUMENTS

| | | | | |
|---|---|---|---|---|
| WO | WO 00/50876 | 8/2000 | | G10N/21/53 |

* cited by examiner

Primary Examiner—Victor J. Taylor
(74) Attorney, Agent, or Firm—Conley Rose, P.C.

(57) ABSTRACT

A method for determining the composition of a fluid by using measured properties of the fluid. One embodiment of the method of the current invention generally comprises: selecting a fluid property that has a response to fluid composition that is linear, or can be approximated as linear; measuring the selected fluid property at a series of specific time intervals; and plotting the measured property as a function of the selected property. In effect, plotting the measured property as a function of fluid composition in an arbitrary set of units. This allows for a in-situ qualitative evaluation of fluid composition by measuring a fluid property that has a known linear relationship to fluid composition. Another embodiment of the present invention further comprises, establishing the endpoints of contamination and plotting the measured properties through these endpoints. Once the endpoints have been established a quantitative evaluation of the fluid composition can be performed. One preferred fluid property that can be used is density.

6 Claims, 5 Drawing Sheets

DETERMINING FLUID COMPOSITION FROM FLUID PROPERTIES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates generally to the evaluation of wellbore fluids, in particular to the determination of the composition of a multi-component fluid. More specifically, the present invention relates to the determination of the fluid composition of a multi-component fluid using measured physical properties of the fluid. This method is particularly useful in in-situ determination of the quality of wellbore fluid samples.

During drilling operations, a wellbore is typically filled with a drilling fluid ("mud"), which may be water-based or oil-based. The mud is used as a lubricant and aids in the removal of cuttings from the wellbore, but one of the most important functions of mud is well control. Hydrocarbons contained in subterranean formations are contained within these formations at very high pressures. Standard over-balanced drilling techniques require that the hydrostatic pressure in the wellbore exceed the formation pressure, thereby preventing formation fluids from flowing uncontrolled into the wellbore. The hydrostatic pressure at any point in the wellbore depends on the height and density of the fluid column of mud above that point. A certain hydrostatic pressure is desired in order to offset the formation pressure and prevent fluid flow into the well. Thus, it is well known in the art to control the mud density and it is often necessary to use high density "heavy" mud to achieve a desired hydrostatic pressure.

Whenever the hydrostatic pressure of the mud is greater than the pressure of the surrounding formation, drilling fluid filtrate will tend to penetrate the surrounding formation. Thus, the fluid in the formation close to the wellbore will be a mixture of drilling fluid filtrate and formation fluid. The presence of fluid filtrate in the formation can interfere with attempts to sample and analyze the formation fluid. As a fluid sample is drawn from the formation at the wall of the wellbore, the first fluid collected may comprise primarily drilling fluid filtrate, with the amount of filtrate in the mixture typically decreasing as collected volume increases. Because the fluid sought to be analyzed is the wellbore fluid, and not the drilling fluid filtrate, it is desirable to collect a sample containing as little drilling fluid filtrate as is possible.

Early formation testing tools were designed to draw in a fixed volume of fluid and transport that volume to the surface for analysis. It was soon realized that the fixed volume was not sufficient to collect a reasonable sample of formation fluid because the sample would be primarily drilling fluid filtrate. To solve this problem, formation testing tools were developed that were able to continuously pump fluid into the testing tool so that sample collection could be controlled by the operator. Using these types of tools, the operators attempt to avoid collecting filtrate in the fluid sample by pumping for a period of time before collecting the fluid sample. The amount of time used to obtain a filtrate-free sample is based on experience or intuition. The problem with this design is there is still no way to determine the quality of the collected sample without pulling the tool to the surface. Therefore, it is desirable to be able to determine the quality of the fluid sample in-situ, with the formation tester still in the well, in order to increase the efficiency and effectiveness of sample collection.

One method that has been used in an attempt to evaluate the quality of a fluid sample downhole is monitoring of a fluid property over time. One such fluid property is fluid density. There are tools available to measure fluid density downhole and plot the measured density as a function of time. As time increases, the measured fluid density in the sample volume changes until it levels out very close to the density of the formation fluid. This leveling out of the density is known as asymptotic convergence and the value of density at this point is the asymptotic value.

It is usually preferred to acquire a sample of the formation fluid when the measured properties of the sample fluid reach asymptotic levels, which indicates that the amount of filtration in the sample cannot be reduced further. The difficulty with this method is that, although an equilibrium between the amounts of formation fluid and drilling fluid filtrate entering the sample volume has been reached, the level of contamination of the fluid mixture may still not be known. For example, if drilling fluid filtrate is migrating into the formation faster than the sample is being drawn, the asymptotic level reached will still have a high percentage of drilling fluid filtrate. Therefore, there is still required a method for in-situ evaluation of a fluid sample that provides more than a qualitative, or low resolution (±10% or more) quantitative, measure of fluid composition.

One method of in-situ evaluation of fluid composition is described in WO 00/50876 and utilizes optical analysis of a fluid sample to evaluate fluid quality. The method utilizes optical density measurements to create data points to which are then used, by curve fitting techniques, to estimate an asymptotic value for the fluid density. This estimated asymptotic value is assumed to be the optical density of the wellbore fluid and is used to determine the amount of drilling fluid filtrate contamination in a sample. Optical density sensors work by transmitting a light of a specific wavelength through a fluid and measuring the optical absorption. The absorption of light as it travels through the fluid is greatly dependent on the type of hydrocarbons present in the fluid and on the wavelength of the light transmitted. Thus, the use of optical density sensors depends greatly on established knowledge of the type of hydrocarbons found in the formation fluid. This method also assumes an additional function for the change in optical density that is used to predict the asymptote and requires that the fluid be analyzed for a significant period of time before the end point (formation fluid property) can be established. Therefore, optical density evaluation does not provide real-time quantitative assessment of the fluid composition. Consequently, there still exists a need for a method for real-time quantitative assessment of the composition of fluid in a wellbore where little or no information may be available about the formation fluid.

The present invention is directed to improved methods for determination of fluid composition in a wellbore that seek to overcome these and other limitations of the prior art.

SUMMARY OF THE PREFERRED EMBODIMENTS

Accordingly, there is provided herein a method for determining the composition of a fluid by using measured properties of the fluid. One embodiment of a method generally comprises: selecting a fluid property that is related to the volume fraction of two or more fluids according to a mixing law; measuring the selected fluid property at a series of specific time intervals and plotting the measured property as a function of the selected property. The selected fluid property preferably has a linear, or approximately linear, relationship to fluid composition, but a property having a non-linear relationship to composition may also be selected if the relationship can be extracted from a single measurement (i.e. only one unknown). In effect, the present method entails plotting the measured property as a function of fluid composition in an arbitrary set of units. This allows for a in-situ qualitative evaluation of fluid composition by measuring a fluid property that has a known relationship to fluid composition.

Another embodiment of the present invention further comprises, establishing the endpoints of contamination and plotting the measured properties through these endpoints. Once the endpoints have been established, a quantitative evaluation of the fluid composition can be performed. The endpoints of contamination (100% drilling fluid filtrate and 100% wellbore fluid) can be determined using any known method.

The selected fluid property would preferably be measurably different for the two components of the fluid, but any fluid property that has a determinable response to levels of contamination may be used. Use of this method for evaluation of formation fluid enables operators to determine the quality and suitability of the sample being collected while the formation testing tool is in the well. Measurements of other fluid properties may also be taken and plotted as a function of the selected fluid property in order to determine the response of those properties to fluid contamination.

Thus the present invention comprises a combination of features and advantages that enable it to substantially advance the fluid evaluation art by providing methods for determining the composition of a fluid mixture using measured properties of the fluid. These and various other characteristics and advantages of the present invention will be readily apparent to those skilled in the art upon reading the following detailed description of the preferred embodiments of the invention and by referring to the accompanying drawings.

BRIEF DESCRIPTION OF THE DRAWINGS

For a more detailed understanding of the preferred embodiments, reference is made to the accompanying figures, wherein.

DETAILED DESCRIPTION OF THE PREFERRED EMBODIMENTS

Figure 1:
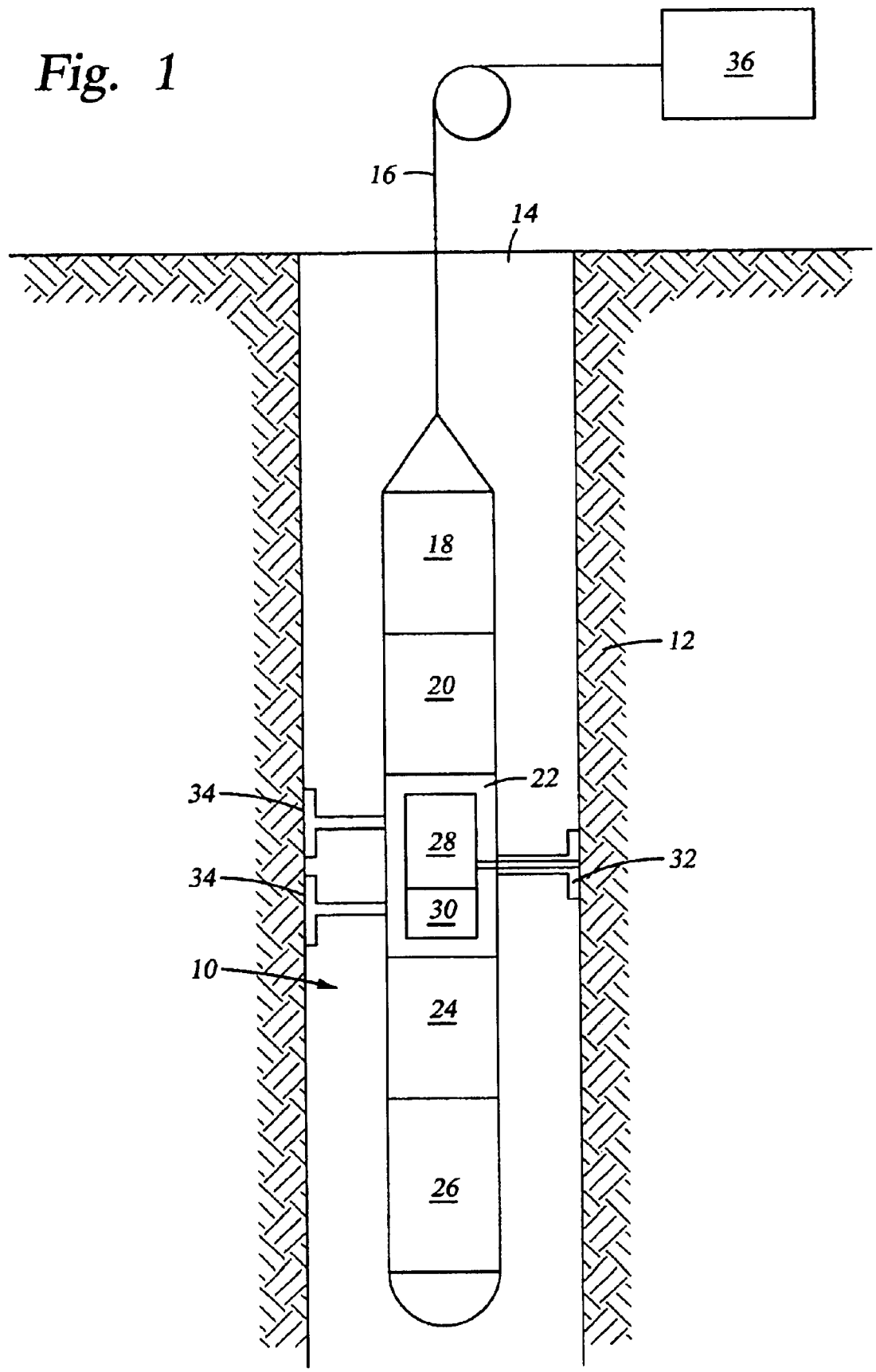
FIG. 1 is a partial sectional view of a prior art formation testing tool.

FIG. 1 shows a prior art formation testing tool 10 for obtaining a fluid sample from a subterranean formation 12 through a wellbore 14. The formation testing tool 10 is suspended in a wellbore 14 by a wireline cable 16 that connects the tool 10 to a surface control unit 36. Formation testing tool 10 comprises an elongated, cylindrical body 18 having a control module 20, fluid acquisition module 22, and fluid storage modules 24, 26. Fluid acquisition module 22 further comprises an extendable fluid admitting probe 32 and extendable tool anchors 34. Fluid is drawn into the tool through the probe 32 by a fluid pumping unit 28. The acquired fluid then flows through fluid measurement module 30 that analyzes the fluid and sends data to surface control unit 36 via the wireline cable 16. The fluid then can be stored in the fluid storage modules 24, 26 and retrieved to the surface for further analysis.

As previously discussed, it is desirable to collect fluid samples after the composition of the fluid includes a sufficient amount of formation fluids. Accordingly, there is provided herein a method for determining the composition of a fluid using data collected by fluid measurement module 30 and analyzed by surface control system 36. The fluid measurement module 30 can be any device capable of measuring a property of the fluid mixture that has a measurable response to the change in fluid composition. Examples of such properties may include: density, resistivity, viscosity, chromatography, radioactivity, dielectric constant, optical density, and magnetic resonance, weight, acoustic impedance, and acoustic velocity. Further, the fluid measurement module 30 preferably has a resolution that allows a number of measurements to be taken between the end points of contamination, i.e. 100% drilling fluid filtrate and 100% formation fluid. These end point values can be assumed to be the maximum and minimum values of the selected fluid property for the given composition.

One embodiment of the present invention uses the measured property of the sample fluid to provide a qualitative indication of the composition of the sample fluid. As shown in FIG. 1, the formation testing tool 10 is positioned at a desired location in a wellbore 14. The fluid pumping unit 28 is activated and draws fluid into the tool. The fluid flows into measurement module 30, which measures a property of the fluid and transmits the measurement results via wireline cable 16 to surface control unit 36. Surface control unit 36 generates a plot of the measured fluid property versus a calculated, normalized filtrate contamination, as explained further below. From this plot a qualitative indication of the level of filtrate contamination in the fluid sample can be obtained.

A second embodiment of the present invention uses the measured property of the sample fluid in conjunction with known densities for one or both end point conditions to provide a quantitative indication of the composition of the sample fluid. This embodiment comprises the same steps as the first embodiment but includes using the known values of the end point fluid properties to provide a scale to the plot of measured fluid property versus normalized filtrate fraction. Therefore, a quantitative indication of the level of filtrate contamination in the fluid sample can be obtained.

One preferred embodiment relies on the selection of a fluid property that can be related to the volume fraction of two or more fluids according to a mixing law. This relationship may be linear but a non-linear relationship is also acceptable if the functional form is known. It is understood that any fluid property that has a relationship to composition that can be extracted from a single measurement (i.e. only one unknown) can be used. Additional unknown properties can also be analyzed provided that unique measurements allow for them to be determined. It is also preferred that the selected property have sufficiently different values for the drilling fluid filtrate and the formation fluid, so that the selected measurement module has sufficient resolution to obtain a reasonable amount of data points between the two endpoints. One preferred fluid property is density.

To illustrate the above described method embodiments, reference will be made to acquiring formation fluid data from a wellbore filled with an oil-based mud. Fluid sampling may be performed with a conventional formation testing tool. One preferable formation testing tool is Reservoir Description Tool as manufactured by Halliburton. A preferred density sensor is the high temperature, high pressure density sensor, as described in U.S. patent application Ser. No. 09/482,793, entitled Downhole Densitometer, and incorporated herein by reference for all purposes.

For fluid mixtures having two primary fluid components, many properties of the mixture are functionally related to the same properties of the component fluids in direct relation to the amount of each component fluid in the mixture. If these properties are known or measured for both the fluid mixture and the component fluids, the composition of the fluid mixture can be determined. For example, the mixture density ($\rho_{mix}$) of a two component fluid mixture can be represented by;

$$\rho_{mix} = \frac{m_1 + m_2}{V_1 + V_2} = \frac{\rho_1 V_1 + \rho_2 V_2}{V_1 + V_2} = \frac{V_1}{V_1 + V_2}\rho_1 + \frac{V_2}{V_1 + V_2}\rho_2 \quad (1)$$

where m, V, and $\rho$ are the mass, volume, and density of the first and second components of the fluid. The above equation can be simplified using f as the volume fraction of one of the components, giving;

$$\rho_{mix} = f\rho_1 + (1-f)\rho_2 = f(\rho_1 - \rho_2) + \rho_2. \quad (2)$$

Therefore, if all three densities are known the volume fraction (f) can be found using the following equation;

$$f = \frac{\rho_{mix} - \rho_2}{\rho_1 - \rho_2}. \quad (3)$$

In many cases, one or more of the densities is not known and it becomes useful to present the density of the fluid mixture ($\rho_{mix}$) as a function of the volume fraction (f);

$$\rho_{mix}(f) = f(\rho_1 - \rho_2) + \rho_2. \quad (4)$$

Taking the derivative of Equation 4 with respect to f gives;

$$\frac{d\rho_{mix}}{df} = (\rho_1 - \rho_2), \quad (5)$$

which shows that an incremental change in the fluid mixture density ($\rho_{mix}$) corresponds to an incremental change in volume fraction (f) by the difference between the two fluid component's densities. Although the exact value of either $\rho_1$ or $\rho_2$ may be unknown, their difference is constant, and therefore the measured data may be plotted on a scale of normalized contamination using the measured density.

Figure 2:
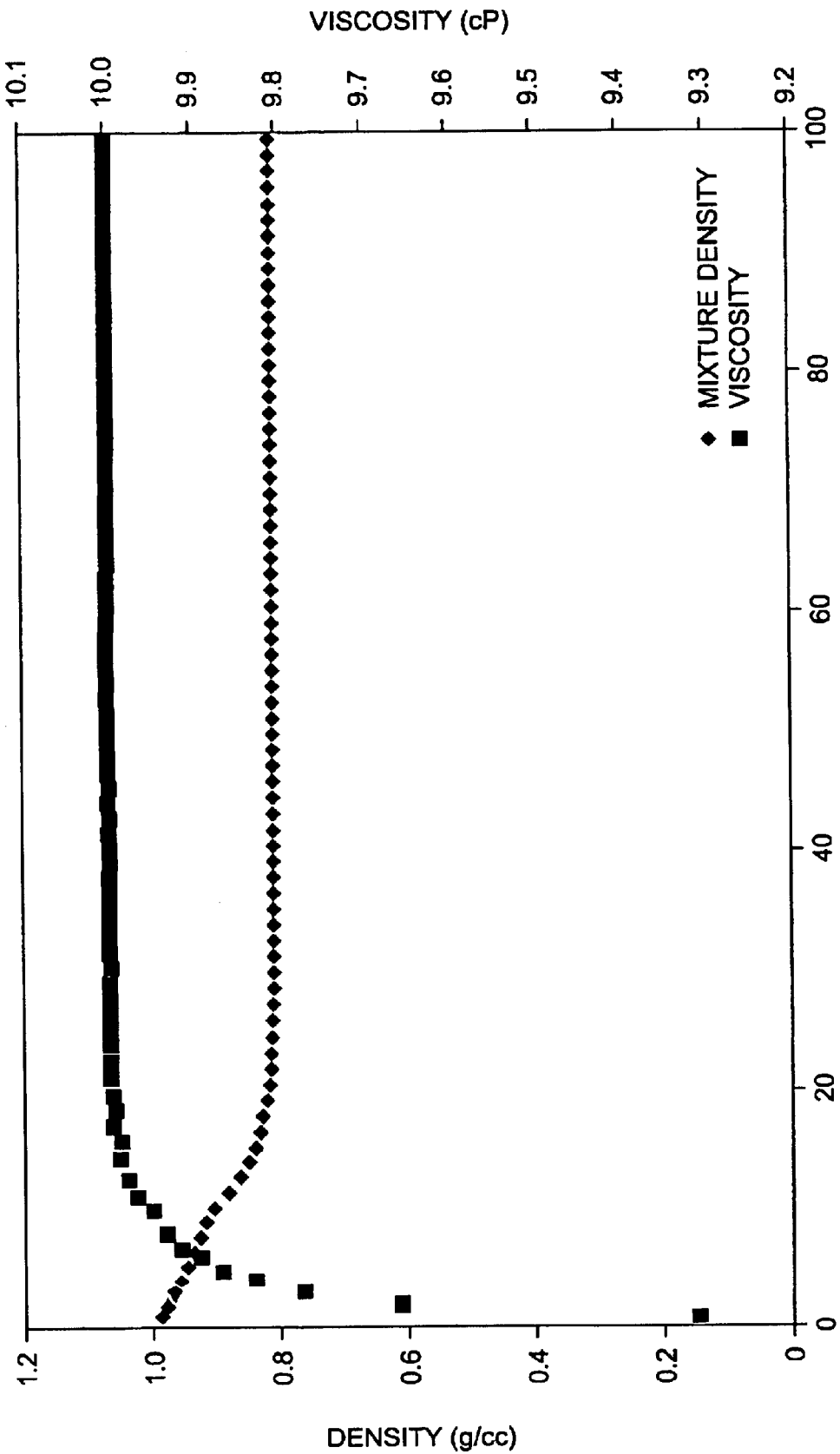
FIG. 2 is a graph of sample fluid density and viscosity versus time.
Figure 3:
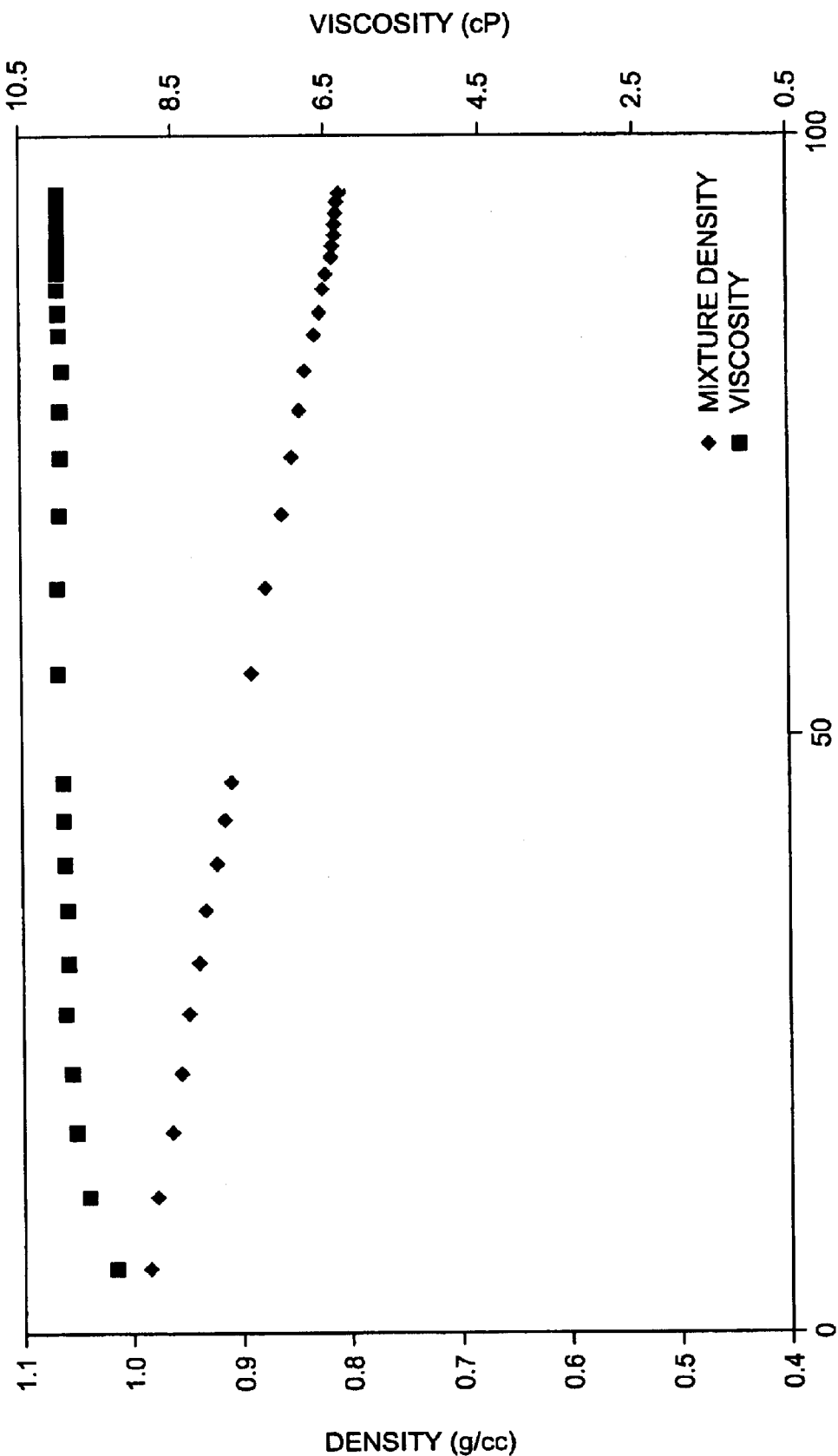
FIG. 3 is a graph of sample fluid density and viscosity versus relative filtrate fraction with unknown endpoints.
Figure 4:
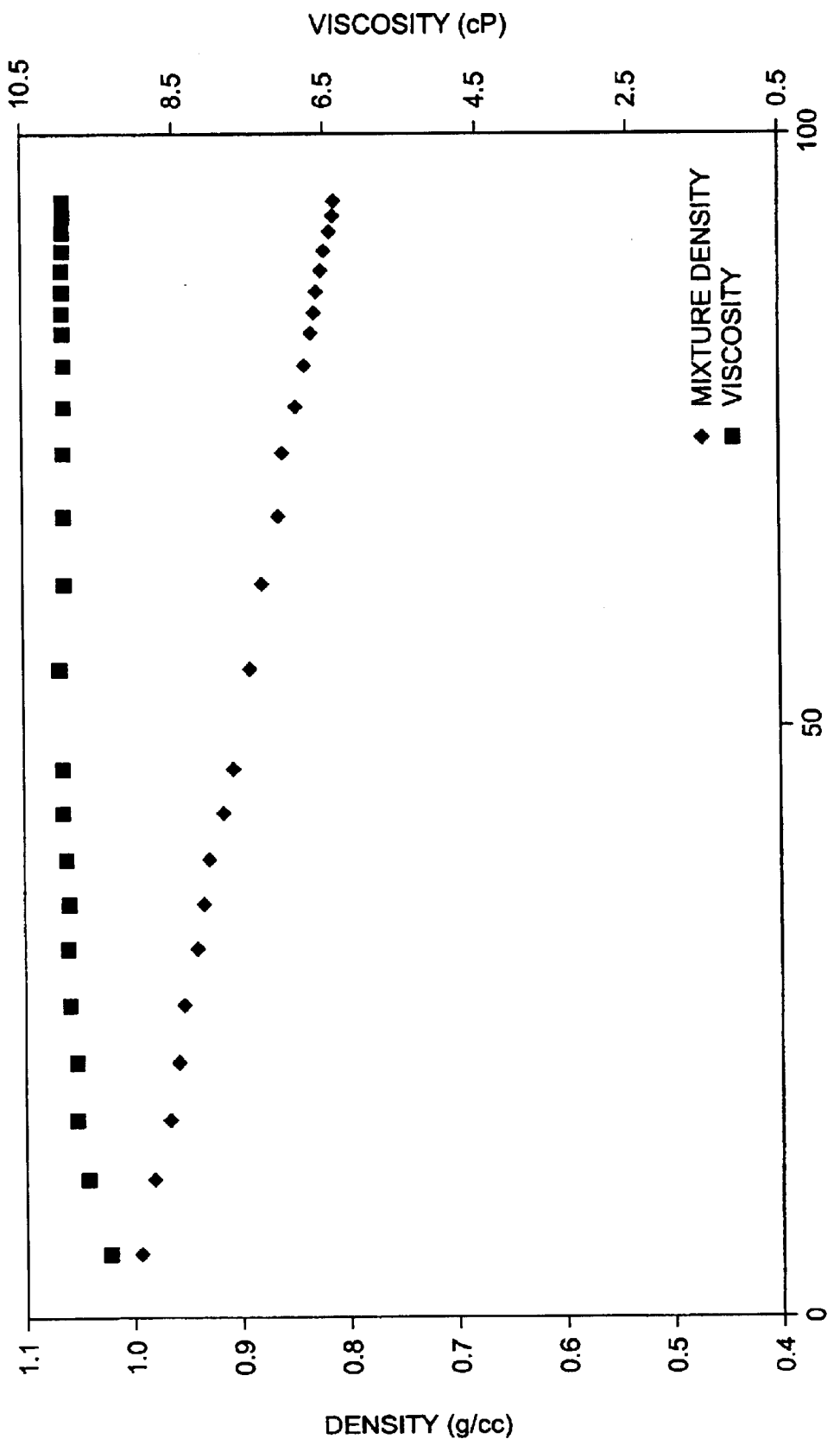
FIG. 4 a graph of sample fluid density and viscosity versus relative filtrate fraction with known endpoints.

Consider, for example, the case of a wellbore fluid that is a mixture of a drilling fluid filtrate with a density of 1.0 g/cc and formation fluid with a density of 0.8 g/cc. FIG. 2 shows the result of typical density and viscosity measurements taken at equally spaced time intervals. FIG. 3, shows the measurements plotted as a function of drilling fluid density. Note that the results are the same as if the independent variable was filtrate contamination in some arbitrary system of units. Hence, this figure can be used to provide a qualitative representation of the fluid composition. FIG. 4 shows that if the end point values of density are known, or can be assumed, the contamination scale is able to be defined and can be used to provide a quantitative representation of the fluid composition.

The end point values of density are the density of the drilling fluid filtrate and the density of the formation fluid. Determination of the density of the drilling fluid filtrate may be assigned based on surface measurements of the mud system. Alternatively, it is also possible to consider the initial fluid density measurement to be essentially the density of the drilling fluid filtrate because the composition of the initial sample will be almost all filtrate. The initial sample may contain a small fraction of formation fluid, so using the initial density measurement as an end point results in consistent overestimation of the level of contamination. Determination of the density of the formation fluid may be ascertained from pressure gradient data, or other methods known in the art.

Figure 5:
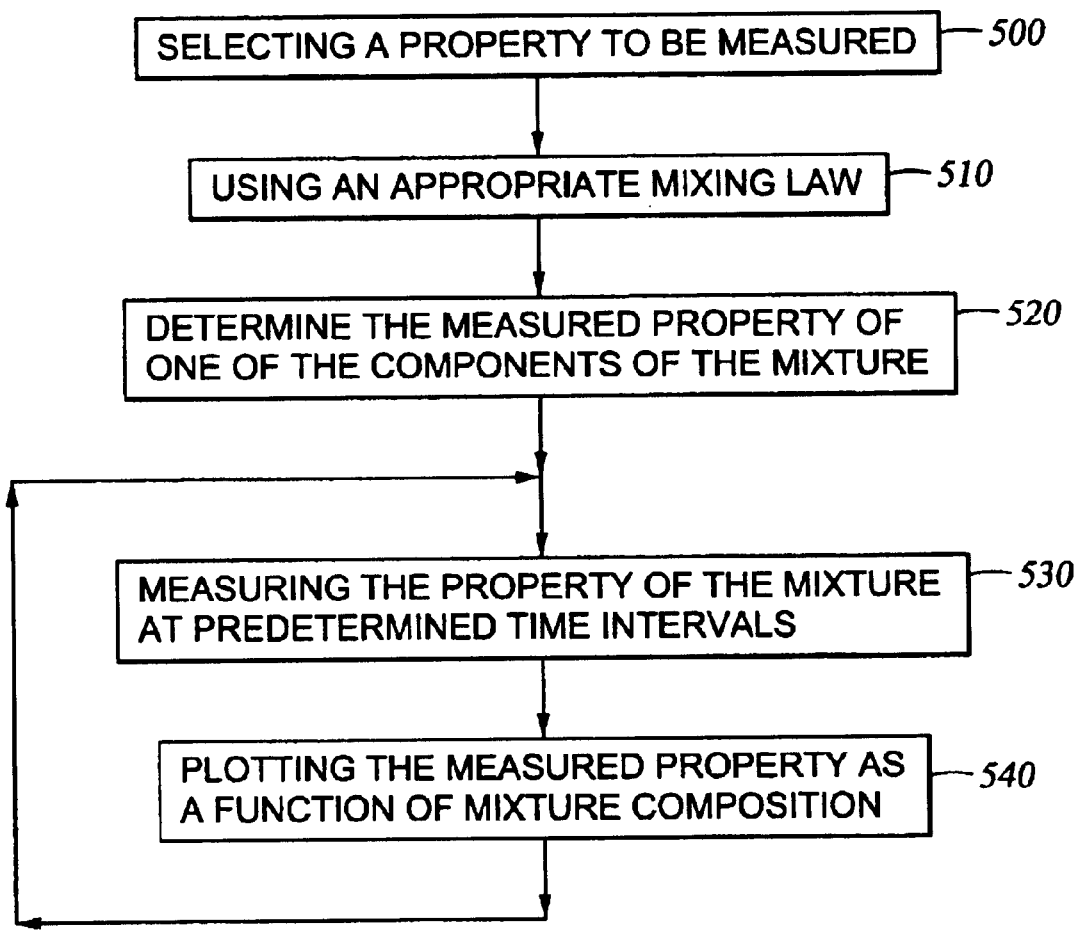
FIG. 5 is a flow chart representing a method for performing analysis.

Thus, by determining the relationship of a property of a mixture to the mixture's components, a real-time, quantitative, indication of the composition of the mixture can be determined. FIG. 5 is a flow chart representing the steps involved in performing analysis using the methods described above. Block 500 represents selecting a property to be measured, taking into consideration such factors as measurability and sensitivity of available instruments. Block 510 represents using an appropriate mixing law to determine the relationship between the measurable property of a mixture and the composition of that mixture. Block 520 represents determining the measured property of one of the components of the mixture, in effect determining the end point of the plot. Block 530 represents measuring the property of the mixture at predetermined time intervals. Block 540 represents plotting the measured property as a function of mixture composition. Block 530 and 540 can be repeated to provide a real-time indication of the mixture composition as a sample is collected.

The embodiments set forth herein are merely illustrative and do not limit the scope of the invention or the details therein. For example, while one preferred measured property is density, it is understood that other fluid properties that have a measurable response to fluid contamination can be used. For example, other fluid properties that may find use in the present invention include resistivity, viscosity, chromatography, radioactivity, dielectric constant, optical density, and magnetic resonance, weight, acoustic impedance, and acoustic velocity. It will be appreciated that many other modifications and improvements to the disclosure herein may be made without departing from the scope of the invention or the inventive concepts herein disclosed. Because many varying and different embodiments may be made within the scope of the inventive concept herein taught, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

It is claimed:

1. A method for determining a composition of a downhole fluid comprising:

measuring the density of the downhole fluid; and determining a normalized fluid contamination using the response of density to fluid contamination, wherein the response is expressible as $$\frac{d\rho_{mix}}{df} = (\rho_1 - \rho_2),$$

wherein $\rho_1$ is the density of a first component of the downhole fluid, $\rho_2$ is the density of a second component of the downhole fluid and, $$\frac{d\rho_{mix}}{df}$$

is the incremental change of the density of the downhole fluid, $\rho_{mix}$, to the change in fluid contamination, f.

2. The method of claim 1 further comprising:
   determining the density of the first component of the downhole fluid;
   determining the density of the second component of the downhole fluid; and
   using the density of the first and second components as end points of a curve created by presenting the measured property versus the actual fluid contamination.

3. A method of determining the composition of a downhole fluid, having a first component and a second component, comprising:
   measuring a density of the downhole fluid; and
   determining a normalized fluid contamination using the measured density; and
   plotting the measured density versus the normalized fluid contamination; wherein the normalized fluid contamination is calculated using the response of density to fluid contamination, wherein the response is expressible as $$\frac{d\rho_{mix}}{df} = (\rho_1 - \rho_2),$$

wherein $\rho_1$ is the density of a first component of the downhole fluid, $\rho_2$ is the density of a second component of the downhole fluid and, $$\frac{d\rho_{mix}}{df}$$

is the incremental change of the density of the downhole fluid, $\rho_{mix}$, to the change in fluid contamination, f.

4. The method of claim 3 further comprising:
   determining a density of the first component of the downhole fluid;
   determining a density of the second component of the downhole fluid; and
   using the densities of the first and second components of the downhole fluid as end points of a curve created by presenting the measured density versus the actual fluid contamination.

5. A method for determining a composition of a fluid comprising:
   pumping fluid through a downhole measurement module;
   measuring the density of the fluid in the downhole measurement module;
   transmitting the measured density data to a control system at the surface; and
   determining a normalized fluid contamination using the measured density and the response of the measured density to fluid contamination; wherein the normalized fluid contamination is calculated using the response of density to fluid contamination, wherein the response is expressible as $$\frac{d\rho_{mix}}{df} = (\rho_1 - \rho_2),$$

wherein $\rho_1$ is the density of a first component of the fluid, $\rho_2$ is the density of a second component of the fluid and, $$\frac{d\rho_{mix}}{df}$$

is the incremental change of the density of the fluid, $\rho_{mix}$, to the change in fluid contamination, f.

6. The method of claim 5 further comprising:
   determining a maximum value of the density;
   determining a minimum value of the density; and
   using the maximum and minimum values of the density as end points of a curve created by presenting the density versus the actual fluid contamination.

* * * * *